United States Patent [19]

Kitajima et al.

[11] 4,452,887

[45] Jun. 5, 1984

[54] INTEGRAL MULTI-LAYERED ELEMENT CONTAINING GLUCOSE OXIDASE FOR DETERMINING GLUCOSE

[75] Inventors: Masao Kitajima; Fuminori Arai; Harumi Katsuyama, all of Saitama, Japan

[73] Assignee: Fuji Photo Film Co., Ltd., Saitama, Japan

[21] Appl. No.: 389,344

[22] Filed: Jun. 17, 1982

[30] Foreign Application Priority Data

Jun. 17, 1981 [JP] Japan .................................. 56-93631

[51] Int. Cl.³ ............................................. G01N 33/66
[52] U.S. Cl. ........................................ 435/14; 422/56; 435/805
[58] Field of Search ...................... 422/56; 435/14, 805

[56] References Cited

U.S. PATENT DOCUMENTS

| | | | |
|---|---|---|---|
| 3,992,158 | 11/1976 | Przybylowicz | 435/14 X |
| 4,042,335 | 8/1977 | Clement | 435/14 X |
| 4,144,306 | 3/1979 | Figueras | 422/56 |
| 4,166,093 | 8/1979 | Smith-Lewis | 422/56 |
| 4,255,384 | 3/1981 | Kitajima | 422/56 X |
| 4,258,001 | 3/1981 | Pierce | 422/56 |
| 4,353,984 | 10/1982 | Yamada | 422/56 X |

*Primary Examiner*—Sidney Marantz
*Attorney, Agent, or Firm*—Sughrue, Mion, Zinn, Macpeak and Seas

[57] ABSTRACT

In a dry-type multilayer liquid analysis material for glucose determination composed of a transparent water-impermeable support having formed thereon in sequence at least a reagent layer containing a reactive component forming a detectable material by the action of hydrogen peroxide, a non-porous light-shielding layer, and a porous spreading layer, the coloring efficiency for colorimetry using the liquid analysis material is improved by incorporating a glucose oxidase enzyme in at least one layer disposed above the reagent layer.

4 Claims, 8 Drawing Figures

INTEGRAL MULTI-LAYERED ELEMENT CONTAINING GLUCOSE OXIDASE FOR DETERMINING GLUCOSE

BACKGROUND OF THE INVENTION

Field of the Invention

This invention relates to liquid sample analysis materials. More particularly, the invention relates to improved dry-type liquid analysis materials which are especially effective in the case of utilizing a glucose oxidase enzyme reaction system forming hydrogen peroxide as a starting reaction for the determination of glucose in a liquid sample, particularly at a relatively high concentration of glucose.

DEVELOPMENT OF THE INVENTION

A determination method where a test material or the reaction product thereof is oxidized using an oxidase enzyme and hydrogen peroxide formed simultaneously with the oxidation is determined by various means has recently become important. The reason therefor is that the determination of hydrogen peroxide can be accurately performed by a colorimeteric determination after a dye-forming reaction using peroxidase or by means of an electrode reaction.

A colorimeteric method based on the foregoing principle using a Trinder reagent is well known. In this method, hydrogen peroxide formed by the action of an oxidase enzyme is reacted with peroxidase to catalyze the oxidative coupling reaction of aminoantipyrine and a phenol and the dye thus formed is colorimetrically determined. The merit of the reaction system is that the same detection system can be utilized for different kinds of oxidase enzymes and the application of the system to various kinds of analysis is being investigated. Among these oxidase enzymes, particularly important enzymes in clinical chemistry are glucose oxidase, cholesterol oxidase, uricase, glycerol oxidase, phosphoglucose oxidase, etc.

An analysis material for clinical analysis composed of an oxidase enzyme and a detection system for formed hydrogen peroxide assembled in an integrated multilayer film or in the form of impregnated strips of filter paper, etc., has been widely used for practical purposes.

In such an analysis material, each composition containing a reagent directly contributing to the detection of a material being analyzed is impregnated in or coated on a filter paper which also acts as a support or a separate support is provided.

Integrated type multilayer analysis materials have various constructions and various functioanal layers are present in the form of laminated layers. Examples of these functional layers are a spreading layer for uniformly spreading a liquid sample as disclosed in, for example, Japanese Patent Publication 21677/78; a light-shielding layer for optically isolation a white light scattering surface for reflection measurement and a colored component present on the upper layer from the formed dye which is detected as disclosed in Japanese Patent Application (OPI) 40191/76 the term "OPI" refers to an application which is unexamined but was published for public inspection); a barrier layer for the selective diffusion of a material as disclosed in Japanese Patent Application (OPI) 3488/77; a detection layer for the detection by mordanting with a formed dye as disclosed in Japanese Patent Application (OPI) 131089/78; an anti-migration layer for preventing a formed dye from diffusing into other layers as disclosed in Japanese Patent Application (OPI) 29700/79; an adhesive layer for improving the adhesion between layers, etc.

Among these layers, a reagent layer is a layer in which a chemical reaction proceeds and the reagent layer can be composed of a single layer or plural layers according to the desired purpose. For example, Japanese Patent Publication 21677/78 describes an analysis material composed of a support having coated thereon a reagent layer and a spreading layer having isotropic porosity, the reagent layer containing salicylic acid which is well known as a stabilization reagent for a blood sample.

For the analysis of a test material which is sparingly soluble in water, such as cholesterol, neutral fat, etc., or a test material such as bilirubin, etc., which is combined with a protein such as albumin, etc., in a sample liquid and is in a state which hardly undergoes diffusion in the layer, an initial treatment such as hydrolysis, dissociation, etc., is performed in the outermost layer to promote diffusion of test material being analyzed in the reagent layer as described in, for example, Japanese Patent Applications (OPI) 137192/77, 24893/78 and 89796/78.

Furthermore, Japanese Patent Application (OPI) 164356/77 discloses that plural reagents used for plural reactions necessary for analyzing one specific component can be separately incorporated in a first reagent layer, a second reagent layer, etc., according to the order of the reactions; however, this technique is useful only for the case that reactions proceed in sequence with a time interval.

Some of these known analysis materials suggest that an oxidase enzyme such as glucose oxidase, etc., can be incorporated therein but the oxidase enzyme is incorporated in a reagent layer in the analysis material in order to prevent the contact of the enzyme with air.

In known multilayer analysis sheets, an example of using a reagent layer as the outemost layer is disclosed in Japanese Patent Application (OPI) 27093/78, but the reagent layer used in the disclosed invention is a specific reagent layer for removing interfering material which would give erroneous analytical results by interfering the whole analysis and for this purpose, the reagent layer is required to be disposed at the outermost layer of the analysis sheet for permitting to pass only the liquid sample.

As described above, various attempts have been made for incorporating a reagent in a layer other than a reagent layer, but the purpose has always been to eliminate a problem specific to each test material and, as a matter of course, the technique shown in the foregoing known references cannot be applied to analytes different from the test materials in these references.

A multilayer analysis material applied to a system of forming a material detectbale by the action of an oxidase enzyme and hydrogen peroxide is described in detail in our prior Japanese Patent Application (OPI) 164356/80. The disclosed multilayer analysis material is composed of a liquid analysis material comprising a water-impermeable and light-transmissive support having thereon a reagent layer containing a reactive composition forming a detectable material by the action of an oxidase enzyme and hydrogen peroxide, a non-porous light-shielding layer, and a fibrous, porous spreading layer.

An analytical procedure using this analysis material includes the steps of bringing a liquid sample having a material to be analyzed dissolved in the sample liquid into contact with the reagent layer, forming hydrogen peroxide in the layer by the action of the oxidase enzyme, and then effecting the oxidative coloring reaction by the action of peroxidase.

Thus, in the case of using such an analysis material containing all the reagents (including an oxidase enzyme) in a reagent layer, the reaction proceeds only very slowly in the analysis of a relatively large amount of a test material (e.g., larger than 300 mg/dl in the case of glucose). In particular, when an aqueous phase is formed in the interior of any layer(s) disposed above the reagent layer or between a space formed by such layer(s), the reaction is even more delayed. This phenomenon is particularly noted when the analysis material has a non-porous layer, e.g., a non-porous light-shielding layer on the reagent layer as illustrated, for example, in Japanese Patent Application (OPI) 164356/80. Such an aqueous phase acts as a barrier to gaseous oxygen since the aqueous phase does not permit to smoothly permeate oxygen therethrough.

In Japanese Patent Publication 45599/81 (corresponding to U.S. Pat. No. 3,983,005), an integral element for the analysis of cholesterol is disclosed. In the disclosed integral element, cholesterol oxidase is incorporated in a spreading layer disposed above a reagent layer. However, the incorporation of cholesterol oxidase in such a spreading layer is esentially required in its nature for the analysis of cholesterol. This is because cholesterol is present in body fluids as free and esterified forms and, for analyzing the total cholesterol, esterified cholesterol should be converted into free cholesterol which should be, in turn, decomposed in the presence of cholesterol oxidase to produce in the element a detectable change that is related to the total cholesterol content of a liquid sample. According to this cholesterol analysis film, cholesterol oxidase is advantageously incorporated into such a spreading layer in part, in addition to a reagent layer. However, there is no recognition or even no suggestion in this publication that the incorporation of cholesterol oxidase in the spreading layer would take important part in acceleration of an enzyme reaction, as will be later explained. Rather, it is art-recognized that the acceleration of the enzymatic method for the analysis of cholesterol is at a stage of hydrolyzing cholesterol esters using cholesterol esterase.

Turning to glucose, it is known that a considerable amount of oxygen is consumed in the enzymatic reaction involving glucose as compared to the system involving, e.g., uric acid. That is, in the case of assaying uric acid by an enzymatic method using uric acid oxidase, only about 2 mg/dl of oxygen is sufficient for oxidizing uric acid, whereas in the case of the glucose assay, glucose content in patinet's blood is often 300 mg/dl or more and, in this case, at least 15 mmol/dl of oxygen is required for oxidizing glucose.

SUMMARY OF THE INVENTION

The inventors have discovered that in a multilayer analysis material employing the coloring reaction of a glucose oxidase enzyme and hydrogen peroxide, the diffusion of a material in a layer, in particular, the diffusion of oxygen, which is necessary for the oxidative action of the oxidase enzyme, is required for the effective progress of the reaction. As the result of investigations in view of the foregoing fact, it has been found that when a glucose oxidase enzyme is incorporated in a layer other than a reagent layer and such layer is above the reagent layer, the reaction rate is determined by the rate of diffusion of oxygen, whereby the speed and the accuracy of the analysis are increased.

An object of this invention is, therefore, to provide a liquid analysis material which provides a quick and accurate measurement by improving the supply of oxygen to a glucose oxidase enzyme and which is particularly suited for the system that is highly probable to consume large amounts of oxygen.

Another object of this invention is to provide a dry-type liquid analysis material giving a good response in concentration-optical density of glucose especially at a relatively high concentration larger than 300 mg/dl of glucose.

Thus, the multilayer liquid analyis material of this invention comprises a water-impermeable and light-transmissive support having formed thereon, in sequence, a reagent layer containing a composition forming a detectable material by the action of hydrogen peroxide, a non-porous light-shielding layer, and a fibrous, porous spreading layer, characterized in that a glucose oxidase enzyme is incorporated in a layer other than and above the reagent layer.

DESCRIPTION OF THE PREFERRED EMBODIMENT

The analytical basis of the analysis material in accordance with this invention is basically the series of reactions first reported by Trinder, that is, the oxidation of glucose is catalyzed by glucose oxidase (EC 1.1.3.4), followed by an oxidative coupling catalyzed by peroxidase (EC 1.11.1.7). The reactions using, e.g., 4-aminoantipyrine as a hydrogen donor and 1,7-dihydroxynaphthalene as a color indicator, proceed as follows.

$$\text{Glucose} + O_2 + 2H_2O \xrightarrow{\text{glucose oxidase}} \text{gluconic acid} + 2H_2O_2$$

In this invention, the term "a layer above the reagent layer" means a layer disposed at the side of the reagent layer remote to the support and above the reagent layer.

As described above, the step of determining the reaction rate by the feed of oxygen involves the oxidation by the material being analyzed by a glucose oxidase enzyme. Based on such knowledge, it has been discovered that when a glucose oxidase enzyme was kept apart from the reagent layer and incorporated in a layer disposed above the reagent layer, such a layer was advantageous in bringing the glucose oxidase enzyme into contact with air, and a very remarkable increase of the reaction rate was occurs.

As the layer disposed above the reagent layer, i.e., the layer disposed at the side of the reagent layer remote to the support, the non-porous light-shielding (or radiation-blocking) layer or the fibrous spreading layer may be used, or if desired or necessary, a function assisting layer or a structure assisting layer (e.g., a timing layer, an adhesive layer, etc.,) to assist the function(s) of these layers may be formed and a glucose oxidase enzyme may be incporated in one or more of these additional layers. As a matter of course, a layer containing only a glucose oxidase enzyme may also be formed above the reagent layer.

The function of the fibrous, porous spreading layer is to supply a sample liquid to the reagent layer at an approximately constant volume per unit area regardless of its applied volume, that is, this layer acts as a spreader for a sample liquid. The action of fibrous, porous spreading layer is then simply to allow a sample liquid placed on the fibrous, porous spreading layer in a measured volume of x $\mu$l, 2x $\mu$l, 3x $\mu$l, . . . to spread on the fibrous, porous spreading layer in proportion to the volume of the sample liquid put thereon through the spreading action inherent in the layer, namely, to spread so as to cover an area of y cm$^2$, 2y cm$^2$, 3y cm$^2$, . . . , respectively and consequently, to render the quantity of the sample liquid to be supplied to the reagent layer per unit area approximately constant. This means that a sample liquid can be analyzed quantitatively without precise measurement of the volume thereof upon analysis, and this has an important significance.

The reagent layer is a layer containing reagents necessary for the colorimetric determination of hydrogen peroxide formed in the oxidation of glucose catalyzed by a glucose oxidase enzyme and generally comprises peroxidase, a hydrogen donor such as an aminoantipyrine and a color indicator such as 1,7-dihydroxynaphthalene.

The non-porous light-shielding (or radiation-blocking) layers refers to a layer that permits effective passage of electromagnetic radiation used to effectively detect an analytical change produced in the analysis material. As has been described above, this non-porous light-shielding layer also bars permeation of oxygen to a considerable extent and the provision of such a layer would create a system in which oxygen reaches the reagent layer only with difficulty.

The timing layer which is optionally provided between the reagent layer and the non-porous light-shielding layer functions as controlling a rate of diffusion in components that diffuse in layers so that a detectable species reaches the reagent layer faster than other components do.

The adhesive layer functions principally to strengthen adhesion force between the reagent layer or the non-porous light-shielding layer and the fibrous, porous spreading layer.

A glucose oxidase enzyme is incorporated in a layer above.

To assist an understanding of the liquid analysis material of this invention, the invention will be explained practically and in detail by referring to the accompanying drawings.

Figure 1:
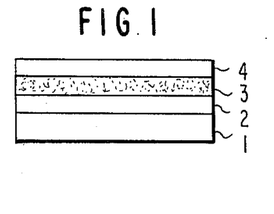
FIG. 1 to FIG. 5 are schematic cross sectional views showing various embodiments of the analysis material of this invention.
Figure 2:
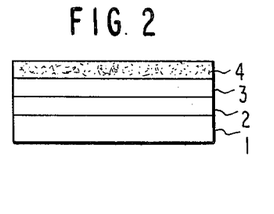

FIG. 1 and FIG. 2 each shows the fundamental structure of the liquid analysis material of this invention, wherein a light-transmissive support 1, a reagent layer 2, a non-porous light-shielding layer 3, and a fibrous liquid sample spreading layer 4 are laminated in this order. A glucose oxidase enzyme is incorporated in the non-porous light-shielding layer 3 (FIG. 1) or in the fibrous liquid sample spreading layer 4 (FIG. 2).

Figure 3:
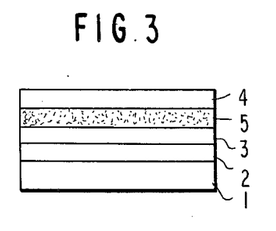

FIG. 3 shows another embodiment of the analysis materail having an adhesive layer 5 disposed under the spreading layer and containing a glucose oxidase enzyme.

Figure 4:
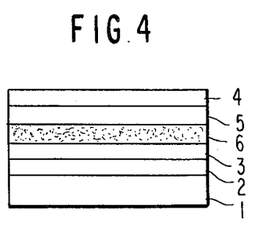

FIG. 4 shows still another embodiment of the analysis material of the structure having an additional layer 6 containing a glucose oxidase enzyme formed between an adhesive layer 5 and a light-shielding layer 3.

Figure 5:
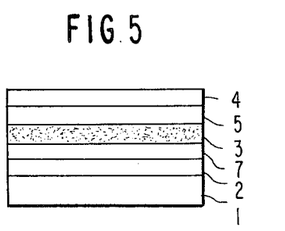

FIG. 5 shows a further embodiment of the analysis material of the structure having a timing layer 7 formed between the reagent layer 2 and the light-shielding layer 3 containing a glucose oxidase enzyme.

A glucose oxidase enzyme is generally incorporated in the foregoing layer by subjecting the material constituting the layer to a soaking treatment in an aqueous solution of the glucose oxidase enzyme or by spraying an aqueous solution onto the material (impregnation and drying). In the case of forming a glucose oxidase enzyme-containing layer (hereinafter often referred to as a glucose oxidase enzyme layer) a layer of the same per se, it is preferred to mix a suitable binder with the enzyme and form the layer on the desired layer, for example, the light-shielding layer 3 in FIG. 4 by coating. In addition. when a glucose oxidase enzyme is incorporated in wetting water usually used in the case of forming a laminate, a glucose oxidase enzyme layer is formed at the interface between layers after finishing laminating.

The fibrous, porous spreading layer used for the analysis material of this invention is composed of a fibrous, porous material such as a paper (e.g., filter paper, synthetic paper, non-wonen fabric, polyethylene pulp, etc.,) or a cloth (e.g., natural or synthetic textile, etc., in particular, plain weave material).

A wide variety of fabrics can be employed as the fibrous, porous spreading layer, and of various fabric tissues, plain weave, which is formed by weaving warp and weft yarns alternately, is preferably used. As for warp and weft which compose plain weave, a desirable count ranges from 20 to 120. Of fabrics having the tissue called plain weave, cotton fabrics of types named close cloth, canequim, broadcloth and poplin are preferably employed. In addition to other natural fibers woven in the same manners as in the above described cotton fabrics (e.g., kapok, flax, hemp, ramie, silk and so on), fabrics obtained by weaving mixed yarns of chemical fiber (e.g., viscose rayon, cupro-ammonium rayon, cellulose acetate, vinylon, polyethylene terephthalate or so on) and cotton fiber in the same manners as in the above described cotton fabrics, and fabrics obtained by weaving chemical fiber yarn in the same manners as in the above described cotton fabrics can be also employed. It is preferred that these fabrics be rendered hydrophilic.

As examples of processes for rendering fabrics hydrophilic, mention may be made of a process in which commercially produced fabrics are washed and rinsed thoroughly with water to remove starch and other processing materials therefrom and optionally they are further dipped with from 1 to 5% aqueous solutions of surface active agents; a process in which surface active agents are made to incorporate into fabrics in proportion of 0.1 to 10% per unit weight of fabric by spraying aqueous solutions of surface active agents onto the fabrics to wet them and then by drying them; etc.

In another type of the process for rendering fabrics hydrophilic, fabrics are wet with hydrophilic polymer solutions, which may contain fine powders such as titanium oxide, barium sulfate and the like, and wetting agents such as glycerine, polyethylene glycol and the like, in addition to hydrophilic polymers such as gelatin, polyvinyl alcohol and the like, and then dried. Hydrophilic polymers are incorporated in fabrics in proportion of from about 0.05 to 10% by weight and preferably from about 0.1 to 5 wt%, per unit weight of fabric. Further details thereon are described in Japanese patent application (OPI) 164356/80 and U.S. Pat. No. 4,292,272.

The non-porous light-shielding layer is a layer formed by dispersing a fine powder such as titanium dioxide, aluminum, barium sulfate, etc., in a water-permeable hydrophilic polymer binder and the thickness thereof is usually from 1 $\mu$m to 100 $\mu$m, preferably from 2 $\mu$m to 20 $\mu$m.

The reagent layer contains a reagent(s) necessary for the colorimetric determination of hydrogen peroxide formed as the result of the reaction of the glucose oxidase enzyme and a specific component in a liquid sample according to an ordinary method. In the reagent layer used in this invention for example, the three components, peroxidase, aminoantipyrine as a hydrogen donor and 1,7-dihydroxynaphthalene as a color indicator, are formed as a layer about 5 $\mu$m to 50 $\mu$m thick using gelatin as a binder.

The hydrogen donor is a compound which is an oxygen acceptor which, in its oxidized state, couples with the color indicator. Representative examples of hydrogen donors include 4-substituted antipyrines as disclosed in U.S. Pat. No. 3,983,005, N,N-disubstituted-o- or -p-phenyenediamines as disclosed in U.S. Pat. No. 3,886,045, 2-hydrazonobenzothiazolines as disclosed in Japanese patent application (OPI) 20471/80, p-halogenophenols as disclosed in Japanese patent application (OPI) 148100/80 and N,N-disubstituted phenylenediamines as disclosed in Ser. No. 352,790 filed Feb. 26, 1982.

As color indicators, various known color forming compounds can be employed. Specific examples of these compounds include monoamines such as aniline, o-toluidine, p-toluidine, etc.; diamines such as o-phenylenediamine, N,N'-dimethyl-p-phenylenediamine, benzidine, dianisidine, etc.; phenols such as phenol, thymol, $\alpha$- or $\beta$-phenol, etc.; polyphenols such as catechol, guajacol, pyrogallol, etc.; aromatic acids such as salicylic acid, gallic acid, etc.; leuco dyes such as leucomalachite green, etc. Further details are described in U.S. Pat. No. 3,983,005 and Ser. No. 352,970 filed Feb. 26, 1982.

A peroxidase is an enzyme which will catalyze a reaction wherein hydrogen peroxide oxidizes another substance. Peroxidase occurs in animals such as leucocyte, milk, liver, spleen, uterus, salivary gland, stomach wall, etc.; in horseradish, potatoes, figtree sap, tabacco plant, yeast, molds, bacteria, etc. Other substances which are not enzymes but which possess peroxidase-like activity are iron sulfocyanate, iron tannate,, potassium chromic sulfate absorbed in silica gel, etc.

If desired or necessary, a timing layer may be formed between the reagent layer and the light-shielding layer. The timing layer is sometimes called as an antimigration layer from its function of bringing a detectable material to the reagent layer relatively faster and such a layer is particularly useful when the detectable material is formed by plural reactions each occurring, in sequence with a time difference.

The timing layer generally contains a mordant as described in e.g., Japanese patent application (OPI) 29700/79, or is composed of the polymer latex described in, for example, Japanese patent applications (OPI) 72622/78 (corresponding to U.S. Pat. No. 4,199,362) and 138432/79 (corresponding to U.S. Pat. No. 4,256,827), which is used as a timing layer for photographic materials.

Figure 6:
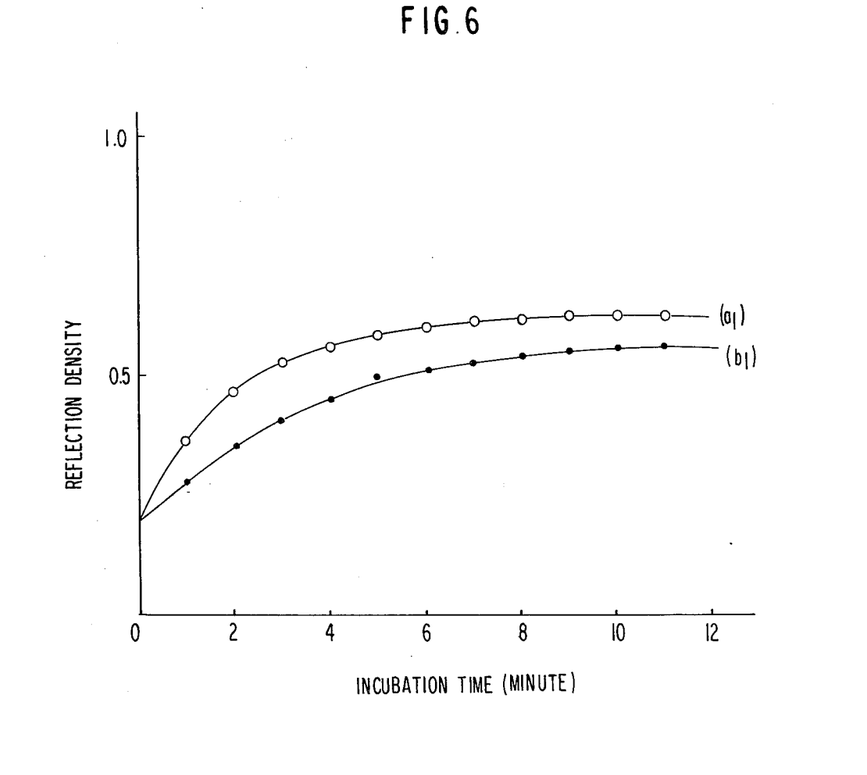
FIG. 6 and FIG. 7 are graphs showing the relation between the reflection density and the incubation time in the case of using glucose having a known concentration.

Also, instead of forming the timing layer as an independent layer as shown in FIG. 6, the timing function may be imparted to the reagent layer by hardening the reagent layer. That is, when the reagent layer is hardened using conventional organic or inorganic hardening agents (solely or as a combination thereof) used for hardening ordinary photographic layers, a timing effect the same as the case of forming a timing layer is obtained. Suitable useful hardening agents are described in, for example, C. E. K. Mees and T. H. James; *The Theory of the Photographic Process;* third edition, pages 55 to 60 (1966) and U.S. Pat. Nos. 3,316,095, 3,232,764 and 3,288,775.

Typical examples of such hardening agents are aldehyde series compounds (e.g., mucochloric acid, formaldehyde, etc.,), active vinyl series compounds (e.g., divinylsulfone, etc.,), active halogen series compounds (e.g., 2,4-dichloro-6-hydroxy-s-triazine sodium salt, etc.,), epoxy series compounds (e.g., 1,4-bis(2',3'-epoxychloroperoxy)butane, etc.,), ethyleneimine series compounds, methanesulfonic acid ester series compounds, carbodiimide series compounds, isoxazole series compounds, inorganic compounds (e.g., chromium alum, etc.,).

Suitable light-transmitting, water-impermeable supports for the analysis material of this invention include known supports having a thickness of 50 $\mu$m to 2 mm, preferably 80 to 300 $\mu$m. Such a support is considered light-transmitting if transparent to visible and near ultraviolet light, e.g., with a wavelength of 290 nm to 400 nm. Suitable examples include synthetic resin films such as polyesters or polycarbonates (e.g., polyethylene terephthalate or polycarbonates of bisphenol A), cellulose esters such as cellulose diacetate, cellulose triacetate or cellulose acetate propionate, polymethyl methacrylate, etc., modified cellulose and glass plates.

The glucose oxidase enzyme used for the liquid analysis materials of this invention may be freely selected from those originated from molds, e.g., *Aspergillus niger*, *Penicillium notatum*, etc.

Such a glucose oxidase enzyme forms hydrogen peroxide by causing a reaction with a substrate and, after subjecting the hydrogen peroxide thus formed to a coloration reaction in a conventional manner, colorimetry is performed.

The formation of hydrogen peroxide is not however, limited to the foregoing example of forming hydrogen peroxide by the direct reaction of a glucose oxidase enzyme and a test material but can also formed by the reaction of a test material and can be similarly formed using a reaction system where a glucose oxidase enzyme is reacted with a secondary reaction product or a tertiary reaction product.

The multilayer analysis material described above is generally used in integrated or laminated form by applying pressure to the liquid sample spreading layer composed of a cloth when the hydrophilic binder in the layers is in a semi-dried state or after wetting the hydrophilic binder with water or water containing a surface active agent.

The multilayer analysis sheet of this invention for analyzing a liquid sample is suitable for determining a specific component in a liquid utilizing a glucose oxidase enzyme reaction system forming hydrogen peroxide by reaction with a substrate. For example, the multilayer analysis sheet of this invention is particularly suitable for the determinations of glucose in body fluids such as urine, blood, etc.

An important feature of the multilayer analysis sheet of this invention is that in the case of a blood sample the components in the blood can be determined without being influenced by the amount of the components, not only is serum but also in whole blood without losing quickness of analysis.

The invention will now be further explained in detail by Examples.

EXAMPLE 1

On a transparent polyethylene terephthalate (PET) film 185 μm thick having a gelatin subbing layer thereon was coated a reagent layer for determining the concentration of glucose in blood having the following composition at a dry thickness of about 15 μm and dried.

| Peroxidase | 25,000 IU |
|---|---|
| 1,7-Dihydroxynaphthalene | 5 parts by weight |
| 4-Aminoantipyrine | 5 parts by weight |
| Gelatin | 200 parts by weight |
| Nonion HS 210 (surface active agent, polyoxyethylene nonyl phenyl ether, made by Nippon Oil and Fats Co., Ltd.) | 2 parts by weight |

On the reagent layer thus formed was coated a light-shielding layer composed of 8 parts by weight of titanium dioxide powder dispersed in 1 part by weight of gelatin at a dry thickness of 15 μm and dried.

Further, an adhesive layer composed of gelatin containing 0.2 part by weight of Nonion HS 210 and 50,000 IU of glucose oxidase was coated on the light-shielding layer at a dry thickness of 5 μm and dried.

The coated film thus formed was uniformly wetted by an aqueous solution of 0.2 wt% nonionic surface active agent (Nonion HS 210) and immediately thereafter a spreading layer composed of a micro filter (FM 120, made by Fuji Photo Film Co., Ltd.) was intimately laminated thereon followed by drying to provide a multilayer analysis sheet for glucose determination.

The analysis sheet thus prepared was cut into a square sheet 15 mm×15 mm and the sheet was mounted on a plastic mount 24 mm×28 mm having a circular opening 10 mm in diameter at the center to provide a multilayer analysis slide for glucose determination.

COMPARISON EXAMPLE 1

Following the same procedure as in Example 1 except that 50,000 IU of glucose oxidase was incorporated in the reagent layer instead of being incorporated in the adhesive layer, a multilayer analysis slide was prepared.

Analysis Regimen

On each of the slides thus prepared was dropped 10 μl of a 7% aqueous albumin solution containing a known glucose concentration (110 mg/dl or 560 mg/dl) and, after incubating at 37° C., the reflection density was measured at 500 nm. The relation between the incubation time and the reflection density is as shown in FIG. 6 and FIG. 7.

Figure 7:
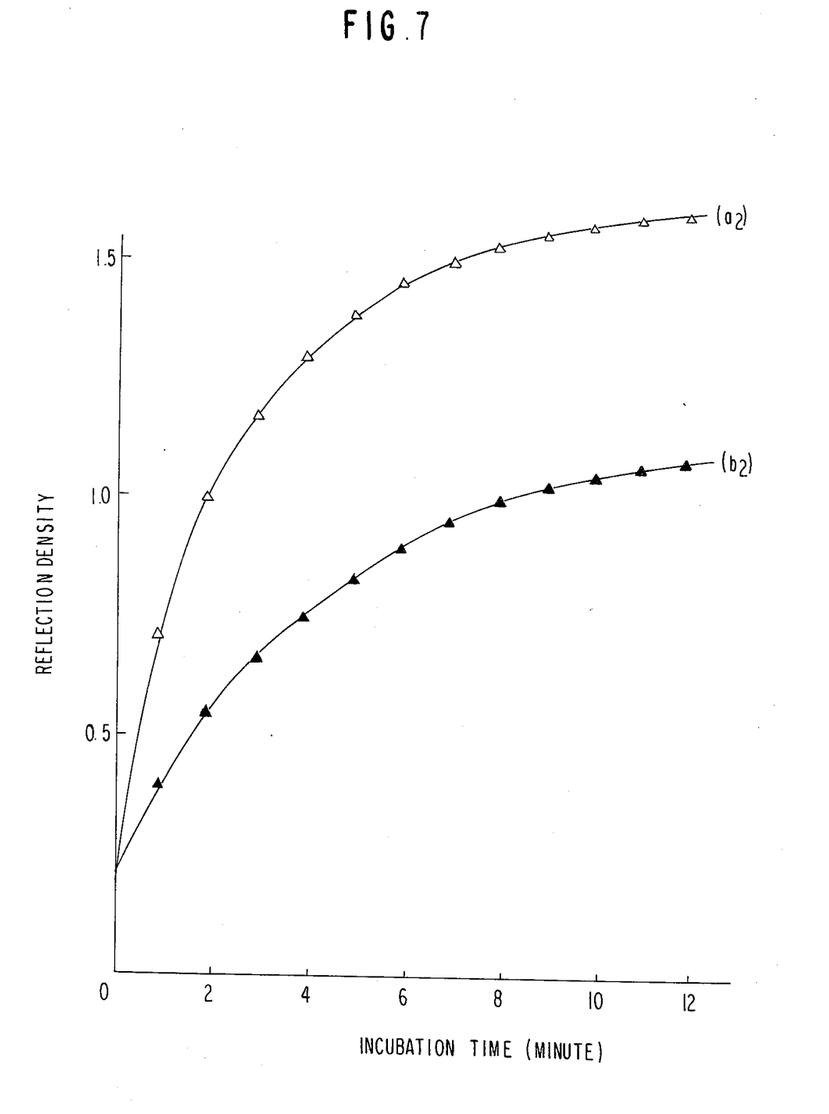

The results when the concentration of glucose was low (110 mg/dl) are shown in FIG. 6 and the results when the concentration was high (560 mg/dl) are shown in FIG. 7.

As can be understood from FIG. 6, when the analysis material of this invention containing glucose oxidase in the adhesive layer was used (Curve $a_1$), the coloring speed was accelerated as compared to the coloring speed obtained using the conventional analysis material (Curve $b_1$). When glucose was used at a high concentration, the difference became more remarkable and when the analysis material of this invention was used (Curve $a_2$) as compared to using the conventional analysis material (Curve $b_2$) and the coloring speed was more remarkably accelerated (FIG. 7).

EXAMPLE 2

Following the procedure of Example 1, a layer containing glucose oxidase was formed between the adhesive layer and the light-shielding layer. That is, a reagent layer having the same composition as in Example 1 was coated on a transparent polyethylene terephthalate film followed by drying and a light-shielding layer having the same composition as in Example 1 was coated thereon and dried. All thicknesses were also as per Example 1.

A gelatin layer containing 50,000 IU of glucose oxidase was then coated on the light-shielding layer at a dry thickness of 15 μm and dried. Furthermore, an adhesive layer composed of gelatin containing 0.2% Nonion HS 210 was coated thereon at a dry thickness of 5 μm and dried.

The coated film thus prepared was uniformly wetted by a 0.2 wt% aqueous solution of nonionic surface active agent (Nonion HS 210) and immediately thereafter a spreading layer composed of a micro filter (FM 120, made by Fuji Photo Film Co., Ltd.) was intimately laminated thereon and dried to provide a multilayer analysis sheet for glucose determination.

The analysis sheet was then cut into a square sheet 15 mm×15 mm and the sheet was mounted on a plastic mount 14 mm×28 mm having a circular opening 10 mm in diameter at the center thereof to provide a multilayer analysis slide for glucose determination.

Analysis Regimen

Testing of whole blood was performed using the multilayer analysis slide thus prepared, i.e., after adding sodium fluoride to a whole blood sample with heparin as a glycolysis inhibitor, a definite amount of the blood was mixed with a small amount of a physiological saline solution containing glucose and, after 2 hours, the concentration of glucose was measured using the multilayer analysis slide. Also, a small amount of each sample was subjected to centrifugal separation and, with the supernatant obtained, the glucose concentration in serum was measured by a conventional hexokinase method. The results of measuring as in Example 1 are shown in Table 1.

From the results shown in Table 1, it was confirmed that there was a good correlation between the glucose concentration and the coloration density.

TABLE 1

| Glucose Concentration (mg/dl) in Serum | Coloration Density |
| --- | --- |
| 0 | 0.170 |
| 98 | 0.392 |
| 185 | 0.535 |
| 248 | 0.591 |
| 352 | 0.743 |
| 472 | 0.897 |

EXAMPLE 3

On a transparent polyethylene terephthalate film 185 $\mu$m thick having a gelatin subbing layer coated thereon was coated a reagent layer for determining the glucose concentration in blood having the following composition at a dry thickness of 15 $\mu$m and dried.

| Peroxidase | 25,000 IU |
| --- | --- |
| 1,7-Dihydroxynaphthalene | 5 parts by weight |
| 4-Aminoantipyrine | 5 parts by weight |
| Gelatin | 200 parts by weight |
| Nonion HS 210 (surface active agent, polyoxyethylene nonyl phenyl ether, made by Nippon Oil and Fats Co., Ltd.) | 2 parts by weight |

On the reagent layer was coated a light-shielding layer composed of 8 parts by weight of titanium dioxide powder dispersed in 1 part by weight of gelatin at a dry thickness of 15 $\mu$m followed by drying.

Furthermore, an adhesive layer composed of gelatin containing 0.2 wt% Nonion HS 210 was coated thereon at a dry thicknes of 5 $\mu$m and dried.

The coated film thus prepared was uniformly wetted with an aqueous solution of 0.2 wt% nonionic surface active agent (Nonion HS 210) and, immediately thereafter a spreading layer composed of a cotton broadcloth (#100) impregnated with glucose oxidase at 25,000 IU/m$^2$ was intimately laminated thereon followed by drying to provide a multilayer analysis for glucose determination.

The analysis sheet thus prepared was the cut into a square sheet 15 mm×15 mm and the square sheet was mounted on a plastic mount 24 mm×28 mm having a circular opening 10 mm in diameter at the center to provide a multilayer analysis slide for glucose determination.

COMPARISON EXAMPLE 3

A comparison analysis slide was prepared in the same manner as in Comparison Example 1 except that the amount of glucose oxidase added to the reagent layer was 25,000 IU per m$^2$.

A coloring test was performed on each of the analysis slides thus obtained in the same manner as in Example 1, whereby the optical reflection density was measured on each glucose concentration. The results are shown in Table 2, which shows the analysis slide obtained per this invention had excellent coloring efficiency.

TABLE 2

| | Glucose Concentration | | |
| --- | --- | --- | --- |
| | 100 mg/ml | 300 mg/dl | 500 mg/dl |
| Example 3 | 0.506 | 0.897 | 1.171 |
| Comparison Example 3 | 0.309 | 1.521 | 0.784 |

EXAMPLE 4

On a transparent polyethylene terephthalate film 185 $\mu$m thick having a gelatin subbing layer thereon was coated a reagent layer for the determination of the glucose concentration in blood composed of the following composition at a dry thickness of 15 $\mu$m followed by drying.

| Peroxidase | 25,000 IU |
| --- | --- |
| 1,7-Dihydroxynaphthalene | 5 parts by weight |
| 4-Aminoantipyrine | 5 parts by weight |
| Gelatin | 200 parts by weight |
| Nonion HS 210 (polyoxyethylene nonylphenol ether, made by Nippon Oil and Fats Co., Ltd.) | 2 parts by weight |

On the reagent layer thus formed was coated an aqueous solution containing 1.6% by weight poly-p-tricyclohexylaminoethylstyrene chloride, 2.2% by weight gelatin, and 0.2% by weight Nonion HS 210 at a dry thickness of 2 $\mu$m to form an antimigration layer.

Furthermore, a layer composed of 25 parts by weight of titanium dioxide, 2 parts by weight of gelatin, and 4,000 IU of glucose oxidase was coated thereon at a dry thickness of 7 m and also an adhesive layer composed of gelatin containing 0.2 wt% Nonion HS 210 was coated thereon at a dry thickness of 5 $\mu$m followed by drying.

The coated film thus obtained was uniformly wetted with an aqueous solution of 0.2 wt% nonionic surface active agent (HS 210) and, immediately thereafter, a spreading layer composed of 100% cotton broadcloth (#100) was intimately laminated thereon and dried to provide a multilayer analysis sheet for glucose determination.

The analysis sheet was cut into a square sheet 15 mm×15 mm and the square sheet was mounted on a plastic mount 24 mm×28 mm having a circular opening 10 mm in diameter at the center to provide a multilayer analysis slide for glucose determination.

Figure 8:
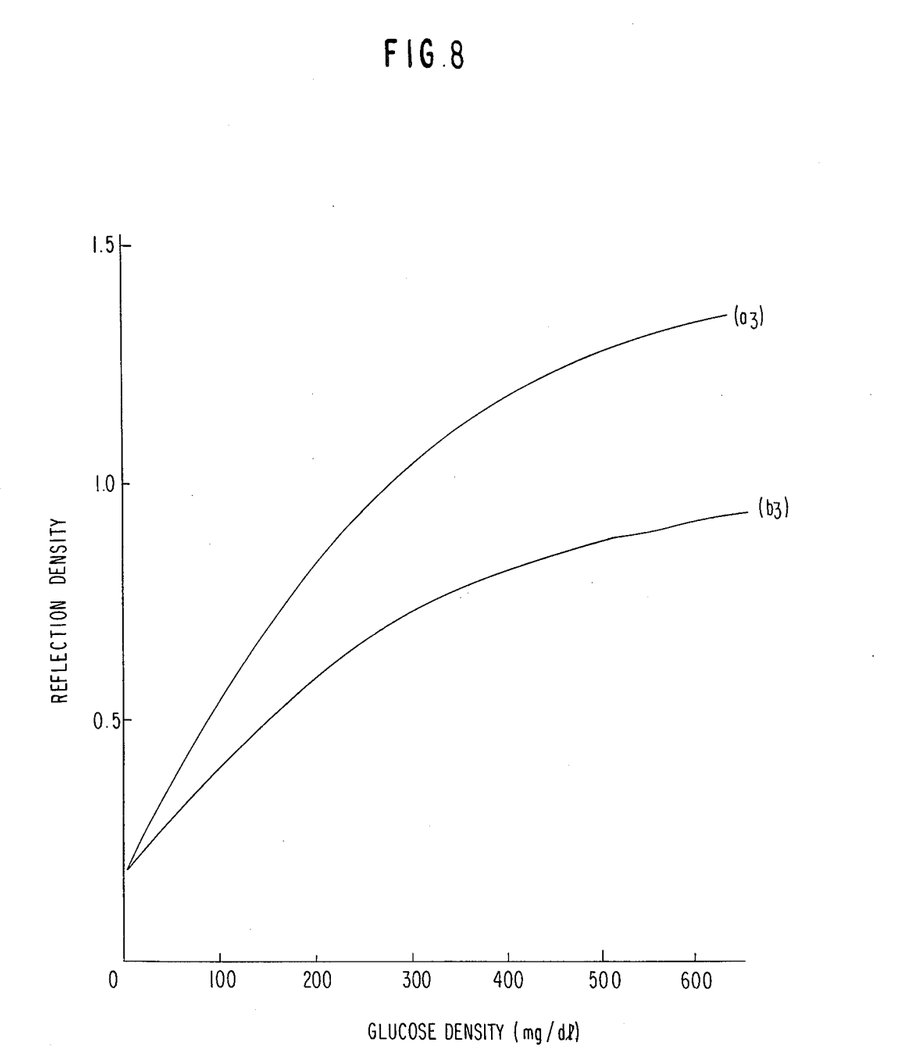
FIG. 8 is a graph showing the relation between the glucose concentration and the optical (reflection) density.

When the coloring property was determined for the multilayer slide for glucose determination thus prepared (see Curve a$_3$ in FIG. 8) together with a comparison analysis material containing glucose oxidase in the reagent layer prepared by the same manner as in Comparison Example 1 (see Curve $b_3$ in FIG. 8), the results shown in FIG. 8 were obtained.

From the results, it was confirmed that the coloring efficiency was greatly improved in the case of the analysis material of this invention where glucose oxidase was incorporated in a layer separated from the reagent layer.

While the invention has been described in detail and with reference to specific embodiments thereof, it will be apparent to one skilled in the art that various changes and modifications can be made therein without departing from the spirit and scope thereof.

What is claimed is:

1. An integral multi-layered element for determining glucose in a liquid sample comprising a water-impermeable light-transmissive support having formed thereon, in sequence, a reagent layer containing a reactive component forming a detectable material by the action of hydrogen peroxide, a non-porous light-shielding layer and a porous spreading layer, wherein a glucose oxidase is incorporated in at least one layer disposed above said reagent layer.

2. The element as claimed in claim 1 wherein a timing layer is formed between said reagent layer and said non-porous light-shielding layer or said layer in which glucose oxidase is incorporated.

3. The element as claimed in claim 1 or 2 wherein an adhesive layer is formed between said non-porous light-shielding layer and said porous spreading layer.

4. The element as claimed in any of claims 1 to 3 wherein said layer disposed above said reagent layer is selected from the non-porous light-shielding layer, the porous spreading layer, the timing layer, and adhesive layer, and the layer in which glucose oxidase is incorporated.

* * * * *